United States Patent [19]

Beuther et al.

[11] 4,399,234

[45] Aug. 16, 1983

[54] PROCESS FOR PREPARING GASOLINE RANGE HYDROCARBONS FROM SYNTHESIS GAS AND CATALYST USED THEREFOR

[75] Inventors: Harold Beuther, Cheswick; Charles L. Kibby, Gibsonia; Thaddeus P. Kobylinski, Prospect; Richard B. Pannell, Allison Park, all of Pa.

[73] Assignee: Gulf Research & Development Company, Pittsburgh, Pa.

[21] Appl. No.: 310,972

[22] Filed: Oct. 13, 1981

[51] Int. Cl.³ .............................................. C07C 1/04
[52] U.S. Cl. .................................................... 518/715
[58] Field of Search ........................................ 518/715

[56] References Cited

U.S. PATENT DOCUMENTS 2,496,265  2/1950  Bilisoly ................................ 518/715

OTHER PUBLICATIONS

Rao et al., Preprints, Division of Fuel Chemistry, American Chemical Society, Mar. 24–28, 1980, pp. 119–126.
Twentieth Annual Spring Symposium of the Pittsburgh Catalysis Society, Program and Abstracts, May 27–29, 1981, Marriott Hotel, Monroeville, Pa.

Primary Examiner—Howard T. Mars
Attorney, Agent, or Firm—Deane E. Keith; Forrest D. Stine; Donald L. Rose

[57] ABSTRACT

Synthesis gas is converted to a gasoline boiling range product high in branched chain paraffins and olefins utilizing a catalyst consisting essentially of (A) silicalite and (B) cobalt, preferably promoted with a Group IIIB or IVB metal oxide on an alumina support of gamma-alumina, eta-alumina or mixtures thereof.

16 Claims, No Drawings

PROCESS FOR PREPARING GASOLINE RANGE HYDROCARBONS FROM SYNTHESIS GAS AND CATALYST USED THEREFOR

REFERENCES TO RELATED APPLICATIONS

U.S. Ser. No. 310,969, filed Oct. 13, 1981 entitled "Conversion of Synthesis Gas to Diesel Fuel and Catalyst Therefor" to Harold Beuther, T. P. Kobylinski, Charles L. Kibby and Richard B. Pannell.

U.S. Ser. No. 310,977, filed Oct. 13, 1981 entitled "Fluid Bed Catalyst for Synthesis Gas Conversion and Utilization thereof for Preparation of Diesel Fuel" to Harold Beuther, T. P. Kobylinski, Charles L. Kibby and Richard B. Pannell.

U.S. Ser. No. 310,973, filed Oct. 13, 1981 entitled "Conversion of Synthesis Gas to Diesel Oil and Gasoline" to Harold Beuther, T. P. Kobylinski, Charles L. Kibby and Richard B. Pannell, which are hereby incorporated by reference.

FIELD OF THE INVENTION

The present invention relates to a process for the preparation of hydrocarbons in the gasoline boiling range and to the catalyst used for such process. More particularly, this invention relates to the conversion of synthesis gas to hydrocarbons in the gasoline boiling range using a silicalite-promoted cobalt on alumina catalyst.

BACKGROUND OF THE INVENTION

The growing importance of alternative energy sources has brought a renewed interest in the Fischer-Tropsch synthesis as one of the more attractive direct and environmentally acceptable paths to high quality transportation fuels. The Fischer-Tropsch synthesis involves the production of hydrocarbons by the catalyzed reaction of CO and hydrogen. Commercial plants have operated in Germany, South Africa and other parts of the world based on the use of particular catalysts. The German commercial operation, for example, concentrated on the use of a precipitated cobalt-thoria-kieselguhr fixed-bed catalyst, and a later modification where MgO, for economy reasons, replaced part of the thoria.

Co-pending U.S. application Ser. No. 310,969 Oct. 13, 1981 entitled "Conversion of Synthesis Gas to Diesel Fuel and Catalyst Therefor" to Beuther, H., Kobylinski, T. P., Kibby, C. L. and Pannell, R. B. describes the selective conversion of synthesis gas to a product high in straight chain paraffins in the diesel fuel boiling range ($C_9$-$C_{21}$) by using a catalyst consisting essentially of cobalt preferably promoted with an oxide of a metal of either Group IIIB or Group IVB of the periodic chart of the elements, supported on a high purity, high surface area, low acid support of gamma-alumina, eta-alumina or mixtures thereof.

SUMMARY OF THE INVENTION

It has now been found in accordance with the present invention, that synthesis gas consisting essentially of CO and hydrogen can be selectively converted to a gasoline boiling range product ($C_5$-$C_{10}$) containing a high degree of branched chain paraffins and branched chain olefins by using a catalyst comprising silicalite-modified cobalt, preferably promoted with a Group IIIB or Group IVB metal oxide, on a high purity, high surface area, low acid support consisting essentially of gamma-alumina, eta-alumina or mixtures thereof. Thus, it has been found that by admixing silicalite with, for example, a cobalt-thoria on gamma-alumina catalyst, which is normally highly selective for the production of a product high in straight chain paraffins in the diesel fuel boiling range, produces a gasoline boiling range product containing hydrocarbons boiling below $C_{10}$ and containing increased amounts of isoolefins and isoparaffins.

Although it is not intended to limit the present invention to any particular theory or mechanism, it is believed that the silicalite isomerizes alpha-olefins present to form internal olefins and isoolefins, which cannot take part in further chain growth thereby limiting the number of upper carbon number fractions while increasing the branching in lighter fractions.

DESCRIPTION OF THE PREFERRED EMBODIMENTS

The catalyst of the present invention comprises an admixture of (A) silicalite and (B) cobalt, preferably promoted by a Group IIIB or Group IVB metal oxide, on a high purity, high surface area, low acidic support consisting essentially of gamma-alumina, eta-alumina or mixtures thereof.

The term "silicalite" as used in the present application is a crystalline silica composition, which can be the so-called "silicalite-1" described in U.S. Pat. No. 4,061,724, the disclosure of which is hereby incorporated by reference, or the "silicalite-2" described in "Nature," Volume 280, Aug. 23, 1979, pages 664–665, the disclosure of which is hereby incorporated by reference. Thus, as described in U.S. Pat. No. 4,061,724, silicalite is a silica polymorph consisting of crystalline silica, which after calcination in air at 600° C. for one hour, has a mean refractive index of $1.39 \pm 0.01$ and a specific gravity at 25° C. of $1.7 \pm 0.05$ grams/cubic centimeter. Silicalite is further described in "Nature," Volume 271, Feb. 9, 1978, pages 512–516, which disclosure is likewise incorporated by reference.

The catalyst of the present invention is prepared by physically admixing crystalline silicalite (A) with (B) a catalyst consisting essentially of cobalt, and preferably, a Group IIIB or Group IVB metal oxide on gamma or eta-alumina, or mixtures thereof described in co-pending U.S. application Ser. No. 310,969 entitled "Conversion of Synthesis Gas to Diesel Fuel and Catalyst Therefor" to Beuther, H., Kobylinski, T. P., Kibby, C. L. and Pannell, R. B. the disclosure of which is hereby incorporated by reference.

Any suitable Group IIIB or IVB metal oxide can be employed in the cobalt catalyst component (B) of the present invention, with oxides of the actinides and lanthanides being preferred. Thus, suitable metal oxides include, for example, $Sc_2O_3$, $Y_2O_3$, $Ac_2O_3$, $Pr_2O_3$, $PrO_2$, $Nd_2O_3$, $Sm_2O_3$, $Eu_2O_3$, $Gd_2O_3$, $Tb_2O_3$, $Tb_4O_7$, $Dy_2O_3$, $Ho_2O_3$, $Er_2O_3$, $Tm_2O_3$, $Yb_2O_3$, $Lm_2O_3$, $UO_2$, $UO_3$, $U_3O_8$, $UO_4$ $2H_2O$, and the like. Especially preferred metal oxides for inclusion in the catalyst of the present invention include $ThO_2$, $La_2O_3$, $CeO_2$, $ZrO_2$, $TiO_2$, $HfO_2$, and unseparated rare earth oxide mixtures high in lanthanum, praseodynium, and neodynium. The most preferred metal oxide for use in the catalyst component (B) of the present invention is thoria and reference will be hereinafter made thereto for example.

The cobalt is supported on either gamma-alumina or eta-alumina or mixtures thereof characterized as having low acidity, a high surface area and high purity. The expression "low acidity" as used in the present application means that the present alumina support catalyst has a Brønsted acidity with $H_o \leq 1.5$ which is less than 5 micromol per gram or about $10^{16}$ acid sites per square meter of surface area. The low acidity of the support of the present invention is required in order to enable the catalyst to provide hydrocarbon product containing low quantities of light gaseous materials ($C_1$–$C_3$).

The cobalt catalyst component of the present invention has a hydrogen chemisorption value of at least 100, preferably from about 125 to about 300 especially 150 or 200 up to 300 micromol hydrogen per gram of total catalyst when measured at 25° C., which values are substantially higher than achieved using an aqueous impregnation solution containing similar metals.

The surface area of the alumina of the present invention is at least 40 or 50 square meters per gram but is not so great as to become unduly microporous so as to permit reactant materials to enter the interstices of the catalyst. A suitable surface area is from about 40 to about 250, preferably from about 150 to about 225 square meters per gram.

As indicated, the alumina must be of high purity. The expression "high purity" as used in the present application means that the alumina contains negligible amounts of sodium, sulphate, silicon, phosphates or other material having a deleterious effect on the metal dispersion or the production of high molecular weight hydrocarbon products. For impurities creating acid sites, less than 5 micromol per gram should be present (about 0.01–0.1 weight percent depending on molecular weight). The deleterious effect of acidity is cracking of intermediate olefins, removing them from chain growth and producing a low molecular weight product.

Catalyst component (B) of the present invention can contain the Group IIIB or IVB metal oxide, e.g. thoria, in amounts of from 0 or about 0.05 to about 100 parts by weight per 100 parts by weight cobalt, preferably from about 0.5 to 25 parts per 100 parts cobalt, with from about 1 to about 10 parts by weight per 100 parts by weight cobalt being especially preferred. The relatively low levels of the Group IIIB or IVB metal oxide control residual catalyst impurities. Thus, such component can be omitted and the catalyst is still operative. In order to omit the Group IIIB or IVB metal oxide from the catalyst, it is merely omitted from the impregnation solution.

The alumina support which is composed of gamma-alumina, eta-alumina or mixtures thereof is present in an amount of from about 10 to about 10,000 parts by weight alumina per 100 parts by weight of cobalt, preferably between about 100 and about 2,000 parts of alumina per 100 parts of cobalt, with from about 200 to about 400 parts by weight of alumina per 100 parts by weight cobalt being especially preferred. Pure gamma-alumina is preferred.

In forming catalyst component (B), the method employed to deposit the catalytic metals onto the alumina support involves the use of a nonaqueous, organic impregnation solution consisting essentially of a soluble cobalt salt and a soluble Group IIIB or IVB salt i.e., thorium salt, in order to achieve the necessary metal loading and distribution required to provide the highly selective and active catalyst of the present invention.

Initially, the alumina support is treated by oxidative calcination of the gamma and/or eta-alumina at a temperature in the range of from about 300° to about 800° C., preferably from about 400° to about 600° C.

Meanwhile, a nonaqueous organic solvent solution of the cobalt and thoria salts is prepared. The nonaqueous organic solvent of the present invention is a non-acidic liquid which is formed from moieties selected from the group consisting of carbon, oxygen, hydrogen and nitrogen, and possesses a relative volatility of at least 0.1. The expression "relative volatility" as used in the present application is defined as the ratio of the vapor pressure of the solvent to the vapor pressure of acetone, as reference, when measured at 25° C.

Suitable solvents include, for example, ketones, such as acetone, butanone (methyl ethyl ketone); the lower alcohols, e.g., methanol, ethanol, propanol and the like; amides, such as dimethyl formamide; amines, such as butylamine; ethers, such as diethylether; hydrocarbons, such as pentane and hexane; and mixtures of the foregoing solvents.

The preferred solvent of the present invention is a mixture of ethanol and acetone, for example, in a weight ratio of about four parts acetone per part of ethanol.

The amount of solvent utilized is an amount that is at least equivalent to the pore volume of the alumina utilized, but not greater than five times the alumina pore volume. For example, a commercially available gamma-alumina useful in the present invention has a pore volume of between about 0.2 to about 0.7 cubic centimeters pore volume per gram of alumina.

Suitable cobalt salts include, for example, cobalt nitrate, cobalt acetate, cobalt carbonyl, cobalt acetylacetonate, or the like with cobalt nitrate and cobalt carbonyl [$Co_2(CO)_8$] being especially preferred. Likewise, any suitable Group IIIB or Group IVB metal salt, such as thorium nitrate, thorium acetate or the like can be employed. In general, any metal salt which is soluble in the organic solvent of the present invention and will not introduce acidity or have a poisonous effect, e.g. a halide, on the catalyst can be utilized. Thorium nitrate is especially preferred.

Next, the calcined alumina support is impregnated in a dehydrated state with the non-aqueous, organic solvent solution of the cobalt and thorium salts. Thus, the calcined alumina should not be unduly exposed to atmospheric humidity so as to become rehydrated.

Any suitable impregnation technique can be employed including techniques well known to those skilled in the art so as to distend the catalytic metals in a uniform thin layer on the catalyst support. For example, the cobalt and thoria can be deposited on the support material by the "incipient wetness" technique. Such technique is well known and requires that the volume of impregnating solution be predetermined so as to provide the minimum volume which will just wet the entire surface of the support, with no excess liquid. Alternatively, the excess solution technique can be utilized if desired. If the excess solution technique is utilized, then the excess solvent present, e.g., ethanol and acetone, is merely removed by evaporation. Thus, the impregnation solution can be added in excess, namely, up to five times the pore volume of the alumina, or can be added using just enough solution to fill the pore volume of the alumina.

Next, the impregnation solution and alumina are stirred while evaporating the solvent at a temperature of from about 25° to about 45° C. until "dryness."

If additional impregnations are needed to obtain the desired metal loading, for example, when the incipient wetness technique is used, the dried catalyst is then calcined in the presence of an oxygen-containing or inert, e.g. nitrogen, gas at a temperature just sufficient to decompose the metal salts and fix the cobalt. Suitable calcination temperatures include those in the range of from about 150° to about 300° C., preferably from about 225° to about 275° C. Such impregnation, drying and calcination can be repeated until the desired metal loading is achieved. If cobalt carbonyl is employed, contact with oxygen must be avoided. Thus, the impregnated catalyst is heated to about 200° C. in an inert gas, e.g., nitrogen, or hydrogen rather than using an oxidative calcination step.

After the last impregnation sequence, the impregnated catalyst is preferably slowly reduced in the presence of hydrogen at a temperature from about 250° to about 400° C. overnight. Although pure hydrogen can be employed for this reduction step, a mixture of hydrogen and nitrogen can be utilized in order to slowly reduce the catalyst. For example, the reduction step can be conducted initially using a gaseous mixture comprising 5% hydrogen and 95% nitrogen, and thereafter, the concentration of hydrogen can be gradually increased until pure hydrogen is obtained so as to slowly reduce the catalyst. Such slow reduction is particularly desirable when the metal salts utilized in the impregnation step are nitrates so as to avoid the dangers involved with an exothermic reaction in which nitrates are given off. Thus, the slow reduction may involve the use of a mixture of hydrogen and nitrogen at 100° C. for about one hour; increasing the temperature 0.5° C. per minute until a temperature of 200° C.; holding that temperature for approximately 30 minutes; and then increasing the temperature 1° C. per minute until a temperature of 350° C. is reached and then continuing the reduction for approximately 16 hours. Such slow reduction process is not required when the cobalt salt is not a nitrate, e.g. cobalt acetate. A zero valent cobalt compound such as cobalt carbonyl can be activated by heating to 200° C. in pure hydrogen overnight.

It is preferred to omit the calcination step following the last impregnation and subject the impregnated catalyst directly to the slow reduction process.

As previously indicated, the catalyst of the present invention is prepared by physically admixing the silicalite component (A) with the cobalt catalyst (B). Any suitable means of combining components (A) and (B) can be utilized including physically admixing particles of each material in the desired proportion and thereafter wetting and comminuting resultant mixture to produce particles having the desired size. Alternatively, each component can be separately comminuted and thereafter admixed to provide the resultant catalyst composite. Preferably, the catalytic components are comminuted after they are combined so as to achieve a uniform particle diameter for each component. However, if desired, the catalyst particle size may be different for each component.

Preferably, the composite catalyst of the present invention has an average particle diameter, which depends upon the type of reactor to be utilized, of from about 0.01 to about 6 millimeters; preferably from about 1 to about 6 millimeters for a fixed bed; preferably about 0.02 to about 0.15 being preferred for a fluidized bed and from about 0.01 to about 0.05 millimeters for a slurry.

The relative amounts of silicalite to cobalt catalyst may be within any desired range, suitably, from about 1 to about 90, preferably from about 20 to about 50 weight percent silicalite based upon the total catalyst weight.

The charge stock used in the process of this invention is a mixture of CO and hydrogen. The source of the CO and hydrogen to be used in the charge stocks for this invention is not critical and can be obtained, for example, by (i) the oxidation of coal or other forms of carbon with scrubbing or other forms of purification to yield the desired mixture of CO and $H_2$ or (ii) the reforming of natural gas. $CO_2$ is not a desirable component of the charge stocks for use in the process of this invention, but it may be present as an inert gas. Sulfur compounds in any form are deleterious to the life of the catalyst and should be removed.

The molar ratio of hydrogen to CO in the charge stock can be, for example, from about 0.5:1 to about 4:1 or higher, e.g., 10:1, preferably, from about 1:1 to about 2.5:1, with 1.5:1 to about 2:1 being especially preferred.

The reaction temperature is suitably from about 160° to about 350° C., preferably from about 175° to about 250° C., and most preferably from about 185° to about 215° C. The total pressure is from about 1 to about 100 atmospheres, preferably from about 1 to about 50 atmospheres, and most preferably from about 1 to about 20 atmospheres. The hydrogen partial pressure is from about 0.1 to about 30 atmospheres, preferably from about 0.5 to about 25 atmospheres, and most preferably from about 1 to about 20 atmospheres.

The gaseous hourly space velocity based upon the total amount of feed is less than 20,000 volumes of gas per volume of catalyst per hour, preferably from about 100 to about 5,000 v/v/hour, with from about 200 to about 2,500 v/v/hour being especially preferred. If desired, pure synthesis gas can be employed or, alternatively, an inert diluent, such as nitrogen, $CO_2$, methane, steam or the like can be added. As used herein, the expression "inert diluent" indicates that the diluent is non-reactive under the reaction conditions herein disclosed or is a normal reaction product.

The synthesis gas reaction using the catalysts of this invention can occur in a fixed, fluid or moving bed type of operation, and the type of operation would not appear to be critical. However, a fixed-bed operation is preferred, and normally the charge gases would be passed downflow through the bed of catalyst and the reaction product would be collected by suitable condensation techniques, after which the products can be separated by fractionation or otherwise.

The invention will be further described with reference to the following experimental work.

EXAMPLE 1

A cobalt catalyst component (B) was made by impregnating pure gamma-alumina (commercially available from Ketjen as CK-300) that had been sieved to pass 100 mesh (0.15 millimeter) and calcined for two hours at 600° C., by a single step, nonaqueous, "wet" impregnation using cobalt nitrates [$Co(NO_3)_2.6H_2O$] and thorium nitrates [$Th(NO_3)_4.4H_2O$] from acetone-ethanol solution in a ratio of acetone/ethanol of approximately 2.5:1. Excess solvent was removed by evaporation at a reduced pressure of approximately 0.01 atmosphere and 25°–30° C. in a rotary evaporator. The catalyst was dried at a temperature of 90° C. with moderate stirring. Melting of the nitrate salts and evolution of water occurred at approximately 50°–60° C. After the water had evolved, the catalyst appeared to be dry.

Prereduction and passivation of the impregnated catalyst was conducted using pure hydrogen at the rate of 720 cm$^3$/gram/hour. The impregnated catalyst was heated to 100° C. at the rate of 5° C. per minute and then maintained at that temperature for about one hour. Next, the catalyst was heated at the rate of 5° C. per minute to a temperature of 200° C. and then held at 200° C. for approximately sixteen hours. The catalyst was then heated at the rate of 10° C. per minute until a temperature of 360° C. was reached and then held at that temperature for twenty-two hours. Next, the catalyst was cooled to below 200° C., purged with nitrogen and further cooled. Air was bled into the nitrogen flow at approximately 1 cubic centimeter of air in 50 cubic centimeters of nitrogen per minute per 5 grams of catalysts for a period of sixteen hours.

The resultant catalyst contained 100 parts by weight cobalt, 18 parts by weight thoria and 200 parts by weight alumina (100Co/18ThO$_2$/200Al$_2$O$_3$). In order to determine cobalt dispersion, hydrogen chemisorption was measured after reduction at 50° C. intervals, from 200° C. to 400° C., for 16 hours at 175 cm$^3$ H$_2$/gram/hour. The chemisorption isotherms were measured at 25° C. after a one hour equilibration at a H$_2$ pressure of about 500 torr (65 kPa); the zero pressure intercept extrapolated from data pointed above 100 torr was taken as the amount chemisorbed. The results are shown in Table I:

TABLE I

| Hydrogen Sorbed at 25° C.[1] (micromol per gram) | | | | | |
|---|---|---|---|---|---|
| Reduction Temperature, °C. | | | | | H/Co |
| 200 | 250 | 300 | 350 | 400 | (350° C. Reduction) |
| 51 | 96 | 154 | 176 | 148 | .066 |

[1]Intercept values for 100-500 mm Hg data, based on weight of reduced catalyst.

The greatest sorption capacity was developed at 350° C. Assuming complete reduction at that temperature, and one hydrogen atom per surface cobalt atom, the values in the last column of Table I estimate the cobalt metal dispersion.

EXAMPLES 2-6

A series of runs were conducted using the catalyst of Example 1 (100Co/18ThO$_2$/200Al$_2$O$_3$) having an average particle size of about 0.4–0.6 millimeter wherein 0.5 gram samples of the prereduced catalyst were initially heated to a temperature of 360° C. in chemically pure hydrogen flowing at the rate of 2400–6000 cm$^3$/gram/hour at the rate of 5° C. per minute for a one hour period, and then held for 65 hours at 360° C.

The hydrogen flow was then reduced to 240 cm$^3$/gram/hour and an equal flow of carbon monoxide was initiated. For those runs where the molar ratio of hydrogen/CO is 2:1, the hydrogen flow rate was increased to 480 cm$^3$/gram/hour.

Sampling was conducted periodically to analyze the products. The conditions utilized in each run and the product distribution is set forth in Table II:

TABLE II

| Ex. No. | 2 | 3 | 4 | 5[2] | 6[3] |
|---|---|---|---|---|---|
| Temp., °C. | 175 | 185 | 195 | 205 | 195 |
| H$_2$/CO | 1:1 | 1:1 | 1:1 | 1:1 | 2:1 |
| CO Flowrate (cm$^3$/gram/hour) | 155 | 155 | 270 | 610 | 270 |
| CO Conversion Rate (cm$^3$/gram/hour) | | | | | |
| To CO$_2$ | 0.2 | 1.1 | 1.6 | 2.9 | (1.3) |
| To Hydrocarbons | 19 | 41 | 61 | 79 | (120) |
| CO Conversion (Percent) | 13 | 27 | 23 | 13 | 44 |
| Product Distribution (Carbon Atom %) | | | | | |
| CH$_4$ | 4 | 5 | 6 | 8 | 9 |
| C$_2$-C$_4$ | 6 | 7 | 8 | 10 | 9 |
| C$_5$-C$_8$ | 23 | 25 | 29 | 34 | 24 |
| C$_9$-C$_{20}$ | 62 | 59 | 50 | 44 | 49 |
| C$_{21}$+ | 5 | 4 | 7 | 4 | 9 |

[2]Separate run
[3]Not aged at 205° C.

The results set forth in Table II indicate that the cobalt catalyst component (B) has good activity and has a high degree of selectivity to C$_9$-C$_{20}$ hydrocarbons in the 50–65% range when the temperature is from 175°–195° C.

EXAMPLE 7

For comparative purposes, a catalyst containing 50 weight percent silicalite and 50 weight percent of the catalyst of Example I is prepared by mixing each component, which has a particle size below 100 mesh, wetting the admixture, comminuting and sieving the resultant mixture to provide uniform 30–40 mesh particles. The silicalite used in this experiment is described in U.S. Pat. No. 4,061,724 and has the X-ray powder diffraction pattern as set forth in column 2, lines 20–28 therein.

The resultant particles were tested for conversion of hydrogen and carbon monoxide in a 1:1 ratio by conducting a series of runs using 0.5 gram samples of the prereduced catalyst initially heated to a temperature of 360° C. in hydrogen flowing at the rate of 2400 cm$^3$/gram/hour at one atmosphere overnight.

The hydrogen flow was then reduced to 480 cm$^3$/gram/hour and an equal flow of carbon monoxide was initiated.

Sampling was conducted periodically to analyze the products, and the conditions utilized included a temperature of 185° C. under a pressure of one atmosphere. The product distribution is set forth in Table III:

TABLE III

| | Co/ThO$_2$/Al$_2$O$_3$ | | Co/ThO$_2$/Al$_2$O$_3$ + Silicalite | |
|---|---|---|---|---|
| Carbon Number | Carbon Atom % | Wt. % N-paraffin In Fraction | Carbon Atom % | Wt. % N-paraffin In Fraction |
| 1 | 4.7 | (100) | 11.3 | (100) |
| 2 | 0.7 | 50 | 1.8 | 75 |
| 3 | 2.5 | 15 | 8.4 | 24 |
| 4 | 3.5 | 20 | 23.2 | 25 |
| 5 | 5.0 | 25 | 23.1 | 35 |
| 6 | 6.1 | 33 | 14.9 | 45 |
| 7 | 6.8 | 46 | 9.0 | 38 |
| 8 | 7.5 | 56 | 4.8 | 22 |
| 9 | 8.5 | 58 | 2.3 | 13 |
| 10 | 9.4 | 62 | 0.9 | 5 |
| 11+ | 45 | | 1 | |

As seen in Table III, the addition of silicalite sharply reduces the amount of C$_{11}$+ product to less than 1 carbon atom percent, whereas without the silicalite the C$_{11}$+ is about 45 carbon atom percent. Moreover, the amount of n-paraffin decreases rapidly in the C$_6$+ fractions produced with the catalyst including the silicalite modifier, whereas the relative amount of n-paraffin produced by the non-silicalite catalyst actually increases. Thus, the n-paraffin content in the $C_7$–$C_{20}$ fraction produced without silicalite is greater than 50 weight percent.

What is claimed is:

1. A process for the conversion of synthesis gas consisting essentially of CO and hydrogen to a product high in branched chain paraffins and olefins in the gasoline boiling range, which comprises contacting said synthesis gas under conversion conditions with a catalyst consisting essentially of an admixture of (A) silicalite and (B) cobalt on a high surface area, high purity, low acidity alumina support of gamma-alumina, eta-alumina or mixtures thereof, said catalyst component (B) having a hydrogen chemisorption value of from about 100 to about 300 micromol of hydrogen per gram of total catalyst when measured at 25° C.

2. The process of claim 1 wherein said catalyst contains from about 1 to about 90 weight percent silicalite based upon the total catalyst weight.

3. The process of claim 2 wherein said catalyst contains from about 20 to about 50 weight percent silicalite.

4. The process of claim 1 wherein said catalyst component (B) comprises cobalt promoted with a Group IIIB or IVB metal oxide.

5. The process of claim 1 wherein said product contains less than about one weight percent hydrocarbons boiling in the $C_{11}+$ range.

6. The process of claim 1 wherein said catalyst contains from about 0.05 to about 100 parts by weight Group IIIB or IVB metal oxide per 100 parts by weight cobalt.

7. The process of claim 6 wherein said catalyst contains from about 1 to about 10 parts by weight Group IIIB or IVB metal oxide per 100 parts by weight cobalt.

8. The process of claim 1 wherein said metal oxide is an oxide of an actinide, a lanthanide or zirconium.

9. The process of claim 8 wherein said metal oxide is thoria.

10. The process of claim 8 wherein said metal oxide is lanthana.

11. The process of claim 1 wherein said support is gamma-alumina.

12. The process of claim 1 wherein the molar ratio of hydrogen to CO is from about 0.5:1 to about 4:1.

13. The process of claim 12 wherein the molar ratio of hydrogen to CO is from about 1:1 to about 2.5:1.

14. The process of claim 1 wherein the synthesis gas conversion conditions include a temperature of from about 160° to about 350° C.

15. The process of claim 14 wherein said temperature is from about 175° to about 250° C.

16. The process of claim 1 wherein the total pressure is from about 1 to about 50 atmospheres.

* * * * *